United States Patent
Zhou

(10) Patent No.: US 12,398,116 B2
(45) Date of Patent: Aug. 26, 2025

(54) TOTAL SYNTHESIS OF ALECTINIB

(71) Applicant: Suzhou Fude Zhaofeng Biochemical Technology Co., Ltd, Suzhou (CN)

(72) Inventor: Lihua Zhou, Suzhou (CN)

(73) Assignee: SUZHOU FUDE ZHAOFENG BIOCHEMICAL TECHNOLOGY CO., LTD, Suzhou (CN)

( * ) Notice: Subject to any disclaimer, the term of this patent is extended or adjusted under 35 U.S.C. 154(b) by 897 days.

(21) Appl. No.: 17/434,077

(22) PCT Filed: Sep. 10, 2020

(86) PCT No.: PCT/CN2020/114478
§ 371 (c)(1),
(2) Date: Aug. 26, 2021

(87) PCT Pub. No.: WO2022/051983
PCT Pub. Date: Mar. 17, 2022

(65) Prior Publication Data
US 2022/0363660 A1    Nov. 17, 2022

(51) Int. Cl.
*C07D 401/04*    (2006.01)
(52) U.S. Cl.
CPC .................. *C07D 401/04* (2013.01)
(58) Field of Classification Search
None
See application file for complete search history.

(56) References Cited

FOREIGN PATENT DOCUMENTS

| EP | 3556754 | * | 10/2019 |
| WO | 2010143664 A1 | | 12/2010 |
| WO | 2012023597 A1 | | 2/2012 |

OTHER PUBLICATIONS

First notice of examination issued in corresponding Chinese Application No. 2020109466801; State Intellectual Property Office; Apr. 9, 2021; 5 pgs.
Search Report issued in corresponding Chinese Application No. 2020109466801; State Intellectual Property Office; Mar. 30, 2021; 5 pgs.
Dover, Lynn G. et al, "Current Status and Research Strategies in Tuberculosis Drug"; Journal of Medicinal Chemistry; 2011, 54, 6157-6165.
Park, Hwangseo et al, "Structure-based virtual screening approach to the discovery of novel PTPMT1 phosphatase inhibitors"; Bioorganic & Medicinal Chemistry Letters 22 (2012) 1271-1275.

* cited by examiner

*Primary Examiner* — Noble E Jarrell
(74) *Attorney, Agent, or Firm* — HAUPTMAN HAM, LLP

(57) ABSTRACT

The present invention relates to a process for preparing alectinib or a pharmaceutically acceptable salt thereof. The present invention also relates to intermediate compounds which are useful in such process and to the preparation of such intermediate compounds.

6 Claims, No Drawings

TOTAL SYNTHESIS OF ALECTINIB

RELATED APPLICATIONS

The present application is a U.S. National Phase of International Application Number PCT/CN2020/114478 filed Sep. 10, 2020.

FIELD OF THE INVENTION

The present invention relates to a process for preparing alectinib or a pharmaceutically acceptable salt thereof. The present invention also relates to intermediate compounds which are useful in such process and to the preparation of such intermediate compounds.

BACKGROUND OF THE INVENTION

Alectinib, chemically known as 9-ethyl-6,6-dimethyl-8-(4-morpholin-4-yl-piperidin-1-yl)-11-oxo-6,11-dihydro-5H-benzo[b]carbazole-3-carbonitrile, is represented by formula I.

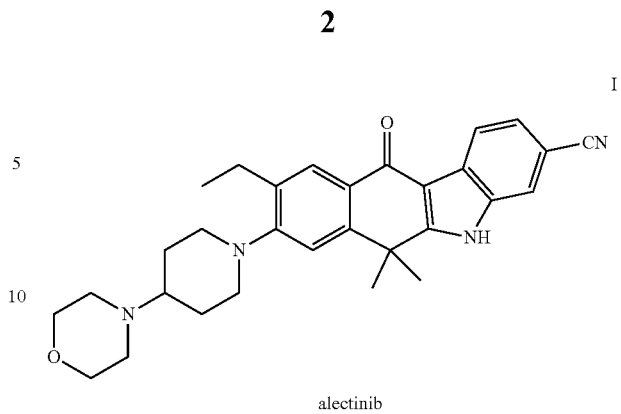

alectinib

Alectinib is a second generation oral drug that selectively inhibits the activity of anaplastic lymphoma kinase (ALK). It is specifically used in the treatment of non-small cell lung cancer (NSCLC) expressing the ALK-EML4 (echinoderm microtubule-associated protein-like 4) fusion protein that causes proliferation of NSCLC cells. Inhibition of ALK prevents phosphorylation and subsequent downstream activation of STAT3 and AKT resulting in reduced tumour cell viability.

The synthesis of alectinib and its hydrochloride salt were described in WO2010143664, WO 2012023597, Bioorganic & Medicinal Chemistry Letters, 2012, 20, 1271-1280, and Journal of Medicinal Chemistry, 2011, 54, 6286-6294. Generally, there are three synthetic routes to alectinib as showned in following scheme:

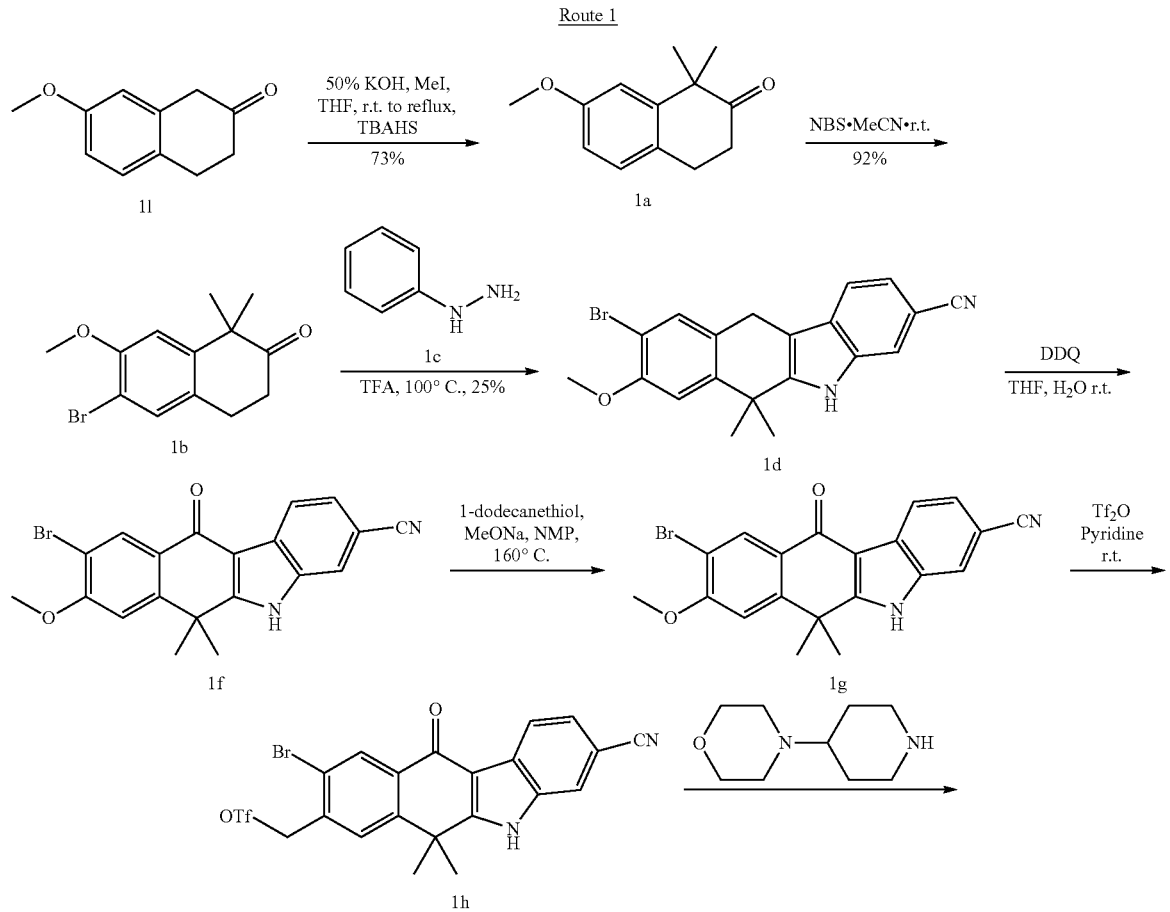

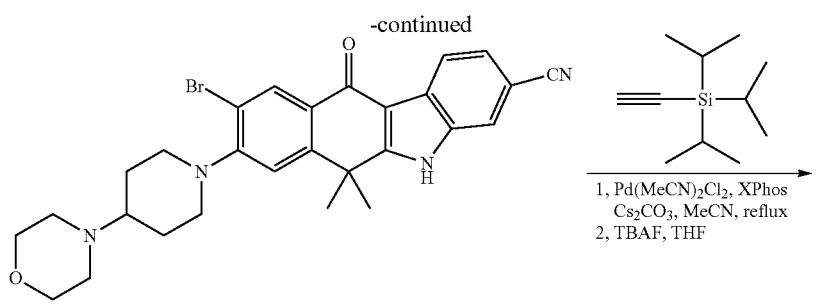
1m
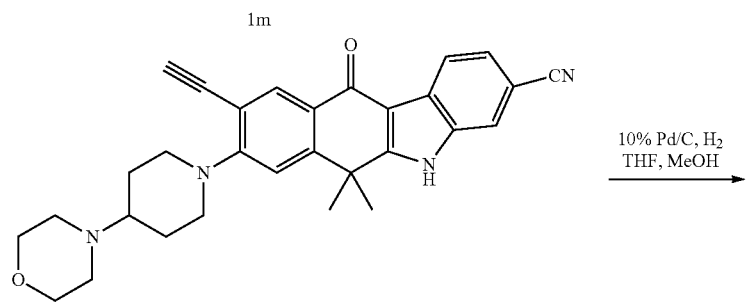
1n
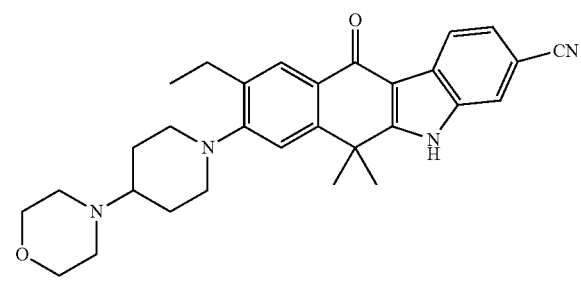
Alectinib
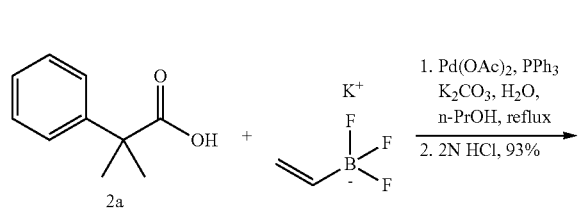
2a
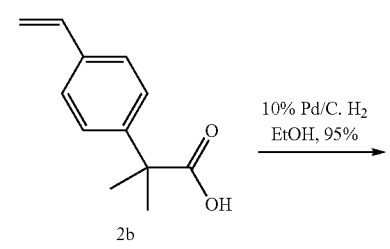
2b
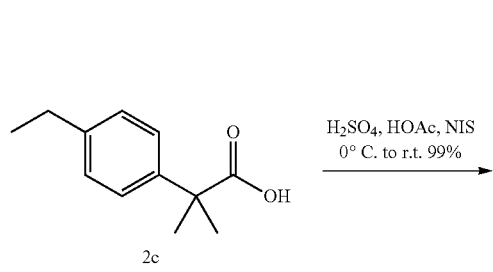
2c
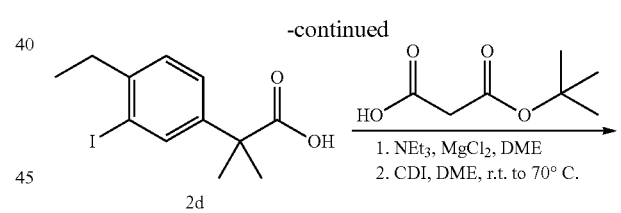
2d
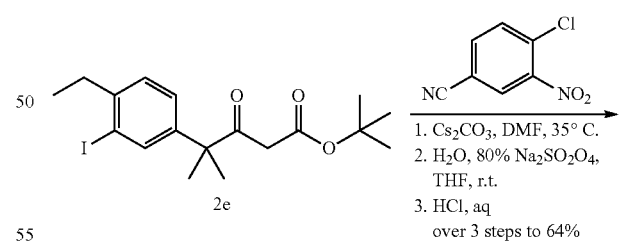
2e
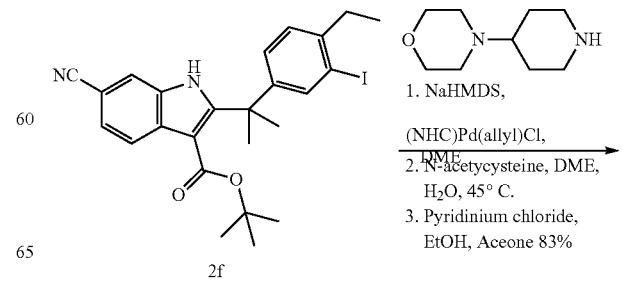
2f

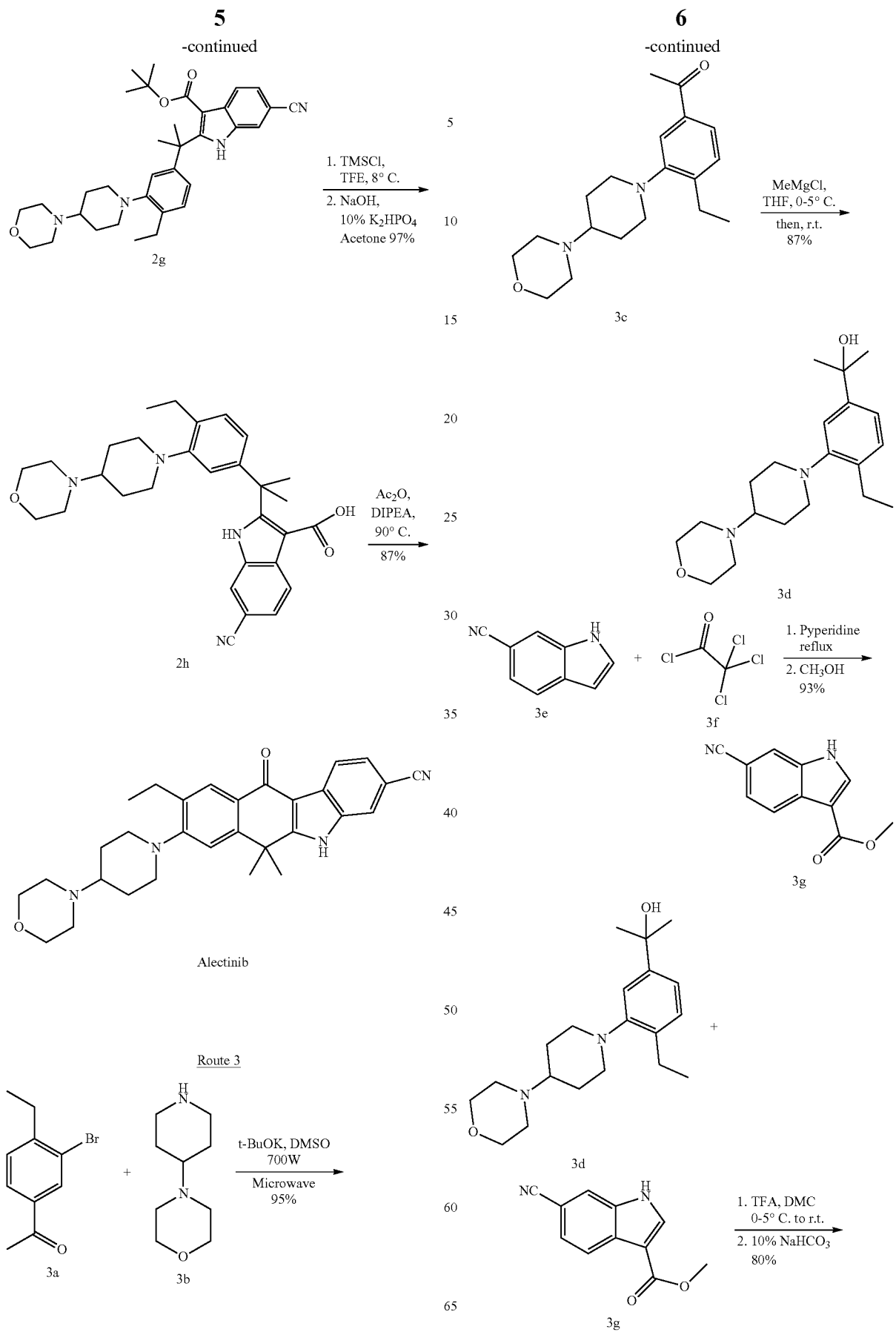

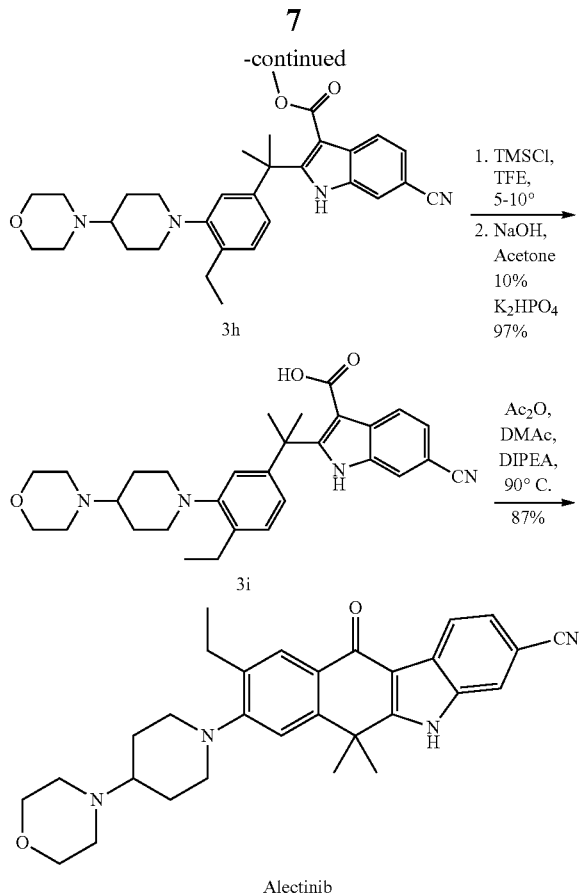

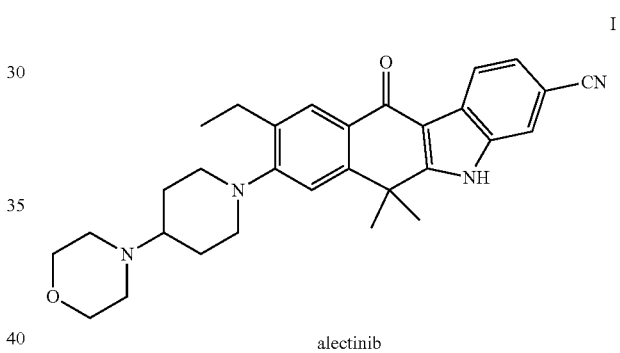

The above mentioned three synthetic routes for alectinib has several disadvantages: high costs inherent to long reaction sequences, expensive reagents and/or catalysts, and inconvenient operation conditions.

Therefore, there still remains a need to improve such process and develop an efficient, simple and industrially viable synthetic route, which can overcome the drawbacks of the prior art.

In order to overcome the problems associated with the prior art, it is herein described a new and improved process which provides alectinib, or a pharmaceutically acceptable salt thereof, in higher yield using cheaper and less toxic reagents.

Definitions

The following definitions are used in connection with the present application, unless it is indicated otherwise.

The term "room temperature" refers to a temperature ranging from about 15° C. to 35° C., preferably to a temperature ranging from about 20° C. to 30° C., more preferably to a temperature of 25° C.

The term "pharmaceutically acceptable salts", includes, for example salts with an inorganic acid, e.g. hydrochloric acid, hydroiodic acid, phosphoric acid, phosphonic acid, sulfuric acid, hydrobromic acid or an organic acid, e.g. a carboxylic acid such as formic acid, acetic acid, citric acid, malic acid, maleic acid, tartaric acid, succinic acid, salicylic acid, trifluoroacetic acid, trichloroacetic acid, oxalic acid, benzoic acid or a sulfonic acid such as p-toluene sulfonic acid or methanesulfonic acid.

The term "alkyl" refers to a straight or branched chain hydrocarbon containing from 1 to 12 carbon atoms. Representative examples of alkyl include, but are not limited to, methyl, ethyl, n-propyl, iso-propyl, n-butyl, sec-butyl, iso-butyl, tert-butyl, n-pentyl, iso-pentyl, neopentyl, n-hexyl, 3-methylhexyl, 2,2-dimethylpentyl, 2,3-dimethylpentyl, n-heptyl, n-octyl, n-nonyl, and n-decyl.

The term "aryl" refers to a monocyclic-ring system or a polycyclic-ring system wherein one or more of the fused rings are aromatic. Representative examples of aryl include, but are not limited to, anthracenyl, fluorenyl, indenyl, naphthyl, and phenyl.

Abbreviations

TEA trimethylamine

DBU 1,8-diazabicyclo[5.4.0]undec-7-ene

DIPEA diisopropylethylamine acac acetylacetonyl

DCE 1,2-dichloroethane

SUMMARY OF THE INVENTION

In one aspect, a method for manufacturing alectinib of Formula I,

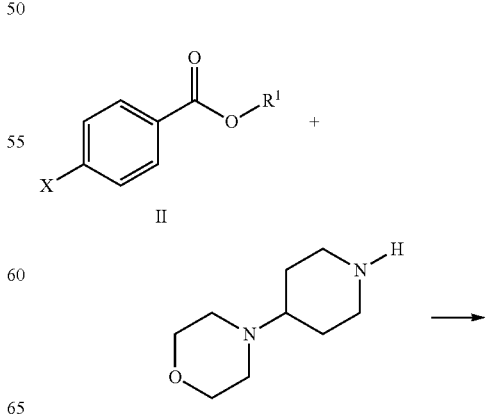

alectinib or a pharmaceutically acceptable salt thereof, which comprises the steps of:

(a) Reacting a compound of formula II with 4-(piperidin-4-yl)morpholine (CAS Registry Number 53617-35-9) in the presence of a base, a copper catalyst and a ligand to form the compound of formula III, -continued

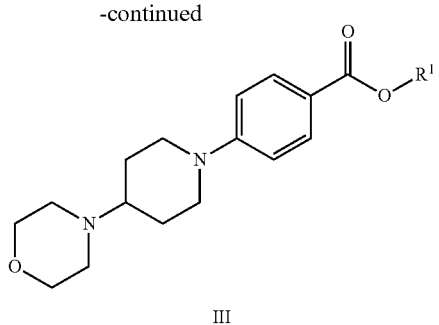

III wherein X is selected from the group consisting of —Cl, —Br, —I, —OSO$_2$Ar, and —OSO$_2$CF$_3$; R$^1$ is selected from any alkyl groups, preferably, R$^1$ is selected from the group consisting of —CH$_3$, —CH$_2$CH$_3$, —C(CH$_3$)$_3$.

(b) Reacting a compound of formula III with CH$_3$CH$_2$Y in the presence of a catalyst to form a compound of formula IV,

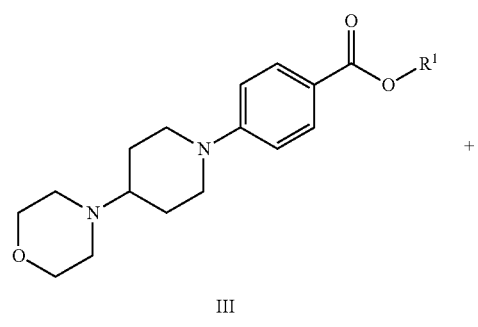

III

CH$_3$CH$_2$Y ⟶

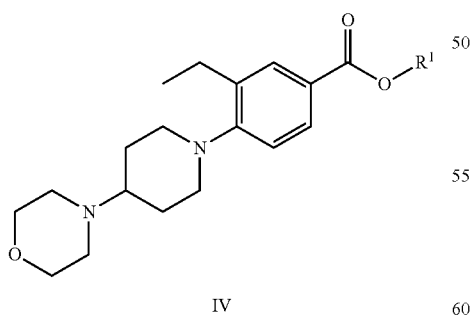

IV wherein Y is selected from the group consisting of —Cl, —Br and —I.

(C) hydrolysis of formula IV resulting in corresponding carboxylic acid, which was then converted to a compound of formula V using SOCl$_2$, PCl$_5$, or POCl$_3$.

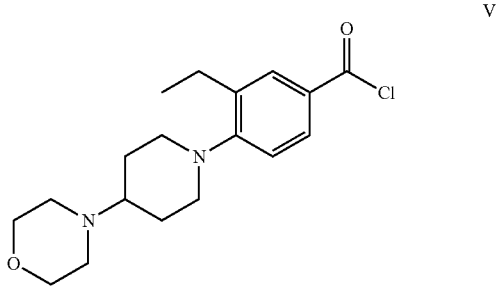 [SMILES: CCc1cc(C(=O)Cl)ccc1N1CCC(N2CCOCC2)CC1]

V (d) Reacting a compound of formula V with 6-cyanoindole (CAS Registry Number 15861-36-6) in the presence of a catalyst to form a compound of formula VI,

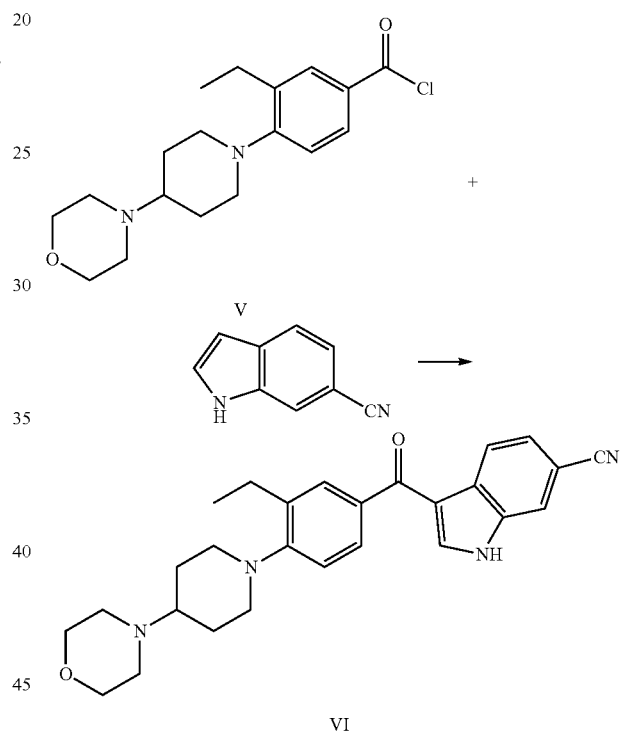

VI (e) Reacting a compound of formula VI with acetone in the presence of a dehydrating reagent and a catalyst to form the alectinib, wherein the dehydrating reagent is selected from MgCl$_2$, AlCl$_3$, CaCl$_2$, 4 Å molecular sieves, and silica gel; the catalyst is selected from chromium and cobalt salts/complex.

The above process is preferably carried out by isolating all intermediate compounds, namely intermediate compounds of formula III, IV, V and VI. Also preferably, the process is carried out without isolating intermediate compound of formula III, IV, V and VI. Even more preferably, the above process is carried out as a one-pot reaction, that is, without the need to isolate any of the intermediate compounds of formula III, IV, V and VI, but completing the whole conversion directly to alectinib, or a pharmaceutically acceptable salt thereof, preferably the hydrochloride salt.

DETAILED DESCRIPTION OF THE INVENTION

The present application is based on the discovery of a novel, alternative approach to synthesizing alectinib. The synthesis described herein allows for the cost-effective preparation of alectinib by reducing production time and cost.

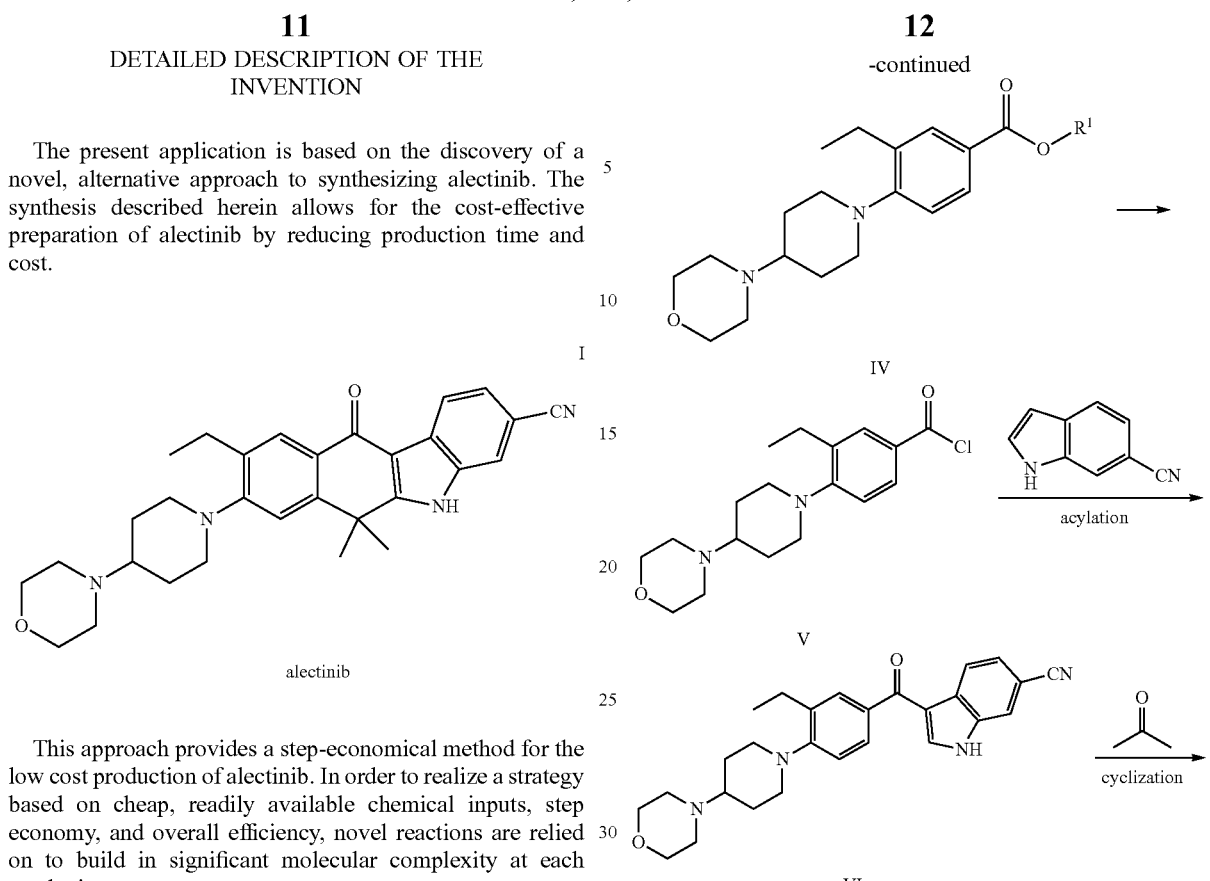

This approach provides a step-economical method for the low cost production of alectinib. In order to realize a strategy based on cheap, readily available chemical inputs, step economy, and overall efficiency, novel reactions are relied on to build in significant molecular complexity at each synthetic step.

In a first aspect, a synthetic method is provided as outlined below in following scheme:

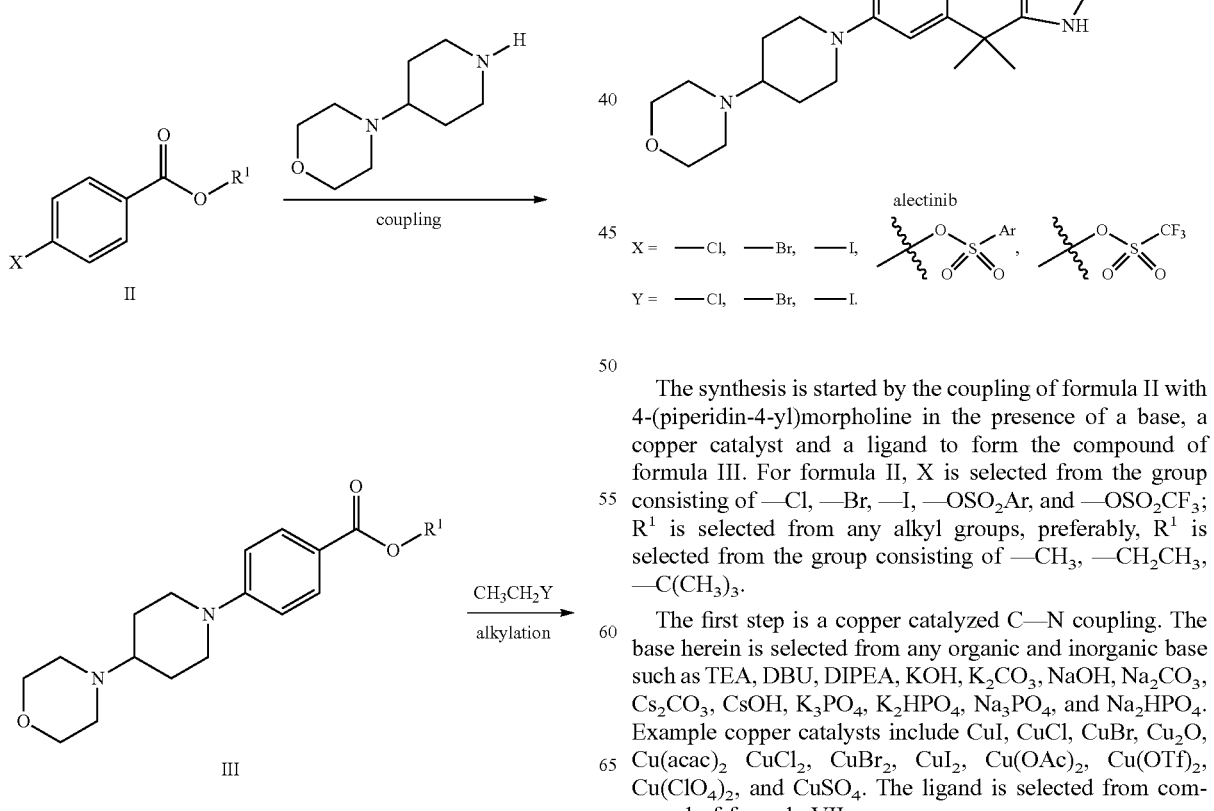

The synthesis is started by the coupling of formula II with 4-(piperidin-4-yl)morpholine in the presence of a base, a copper catalyst and a ligand to form the compound of formula III. For formula II, X is selected from the group consisting of —Cl, —Br, —I, —OSO$_2$Ar, and —OSO$_2$CF$_3$; R$^1$ is selected from any alkyl groups, preferably, R$^1$ is selected from the group consisting of —CH$_3$, —CH$_2$CH$_3$, —C(CH$_3$)$_3$.

The first step is a copper catalyzed C—N coupling. The base herein is selected from any organic and inorganic base such as TEA, DBU, DIPEA, KOH, K$_2$CO$_3$, NaOH, Na$_2$CO$_3$, Cs$_2$CO$_3$, CsOH, K$_3$PO$_4$, K$_2$HPO$_4$, Na$_3$PO$_4$, and Na$_2$HPO$_4$. Example copper catalysts include CuI, CuCl, CuBr, Cu$_2$O, Cu(acac)$_2$, CuCl$_2$, CuBr$_2$, CuI$_2$, Cu(OAc)$_2$, Cu(OTf)$_2$, Cu(ClO$_4$)$_2$, and CuSO$_4$. The ligand is selected from compound of formula VII,

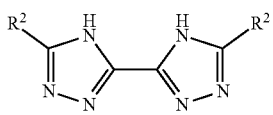

VII

Wherein R² is selected from any alkyl and substituted/ unsubstituted aryl groups. Preferably, R² is selected from methyl, ethyl, propyl, isopropyl, tertbutyl; and substituted/ unsubstituted anthracenyl, fluorenyl, indanyl, indenyl, naphthyl, and phenyl groups. Some examples of formula VII are listed as following (L1-L10):

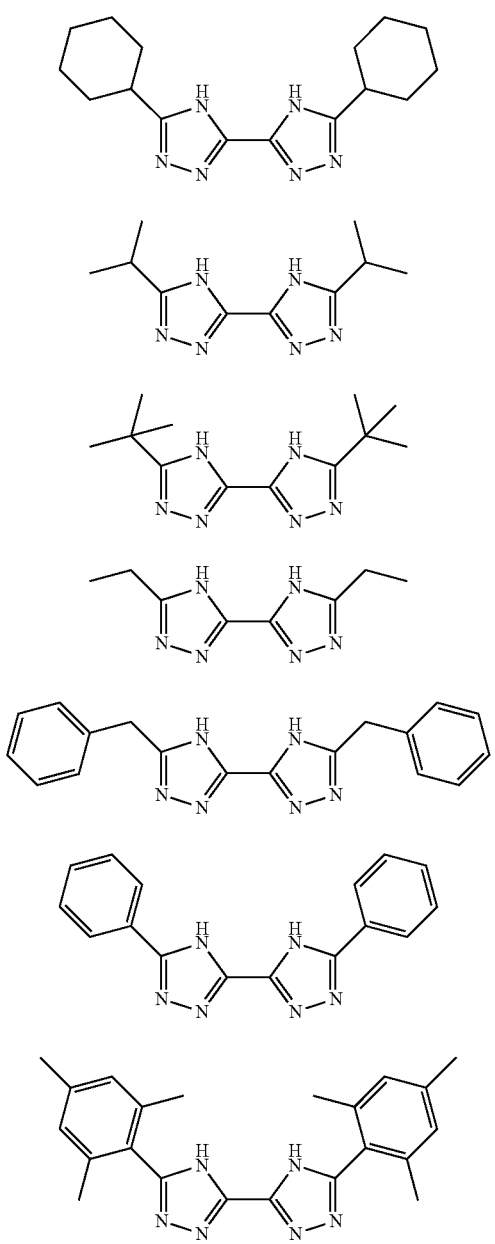

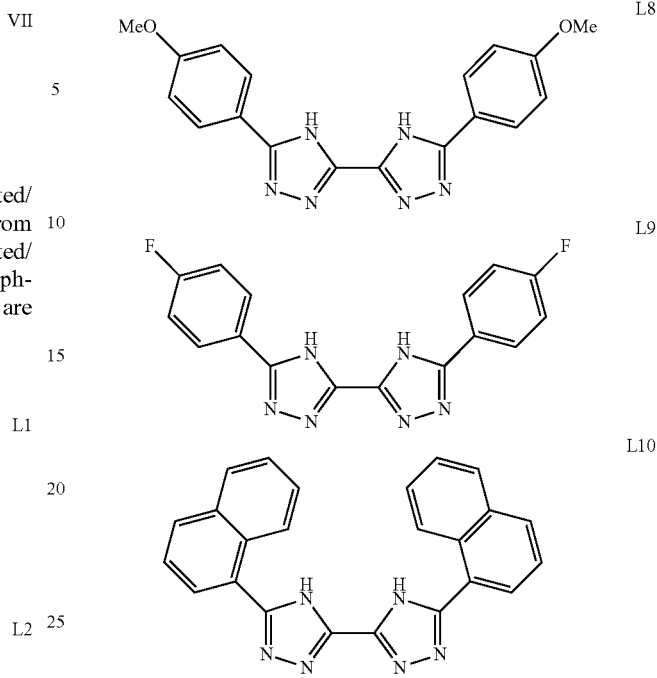

The compound of formula VII is firstly employed as the ligand in the coupling reaction of C—N bond. The compound of formula VII is readily available and it shows high selectivity and efficiency in the coupling reaction. It can be applied to a wide range of substrates with different substituents.

The compound of formula VII can be prepared by the reaction of an aldehyde, oxalohydrazide and ammonia acetate as showed in following scheme:

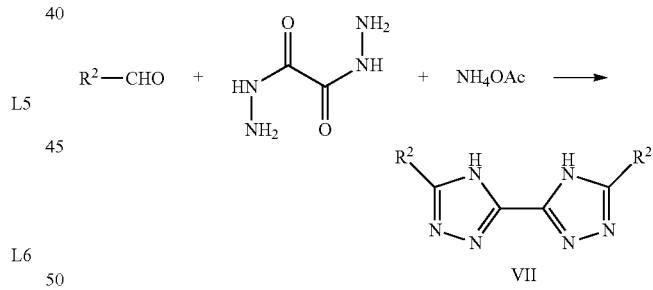

The second step of the synthesis is the Friedel-Crafts Alkylation of formula III with CH₃CH₂Y in the presence of a catalyst to form a compound of formula IV. Herein Y is selected from the group consisting of —Cl, —Br and —I, and the catalyst is selected from Lewis acids that are used for Friedel-Crafts alkylations, such as AlCl₃ BeCl₂, CdCl₂, BF₃, BBr₃, GaCl₃, AlBr₃, FeCl₃, TiCl₄, SnCl₄, SbCl₅, lanthanide trihalides, and alkylaluminum halides (AlRX₂).

Next, the ester group of formula IV is hydrolyzed to carboxylic acid, which is then converted to a compound of formula V by reacting with SOCl₂, PCl₅, or POCl₃.

The compound of formula V is then treated with 6-cyanoindole in the presence of a catalyst to form a compound of formula VI, which is a typical Friedel-Crafts acylation. The catalyst is selected from Lewis acids that are used for Friedel-Crafts acylations, such as AlCl₃, AlBr₃, lanthanide triflates, zeolites, protic acids (e.g., H₂SO₄, H₃PO₄), FeCl₃, ZnCl₂, polyphosphoric acid.

The last step of the synthesis is the cyclization of the compound of formula VI with acetone in the presence of a dehydrating reagent and a catalyst to form the alectinib, wherein the dehydrating reagent is selected from MgCl₂, AlCl₃, CaCl₂, 4 Å molecular sieves, and silica gel; the catalyst is selected from chromium and cobalt salts, such as CrCl₃, CrF₃, CrBr₃, Cr(NO₃)₃, CoCl₃, CoF₃, CoBr₃, Co(NO₃)₃.

Example 1

As illustrated in following scheme, the example synthesis of alectinib began with the coupling of methyl 4-bromobenzoate (II-1) and 4-(piperidin-4-yl)morpholine. The resulted compound of formula III was alkylated by bromoethane to form the compound of formula IV, which was converted to the compound of formula V by hydrolysis and chlorination. The compound of formula V underwent Friedel-Crafts acylation with 6-cyanoindole, leading to the formation of formula VI. Finally, the cyclization of the compound of formula VI with acetone in the presence of a dehydrating reagent and a catalyst led to formation of alectinib.

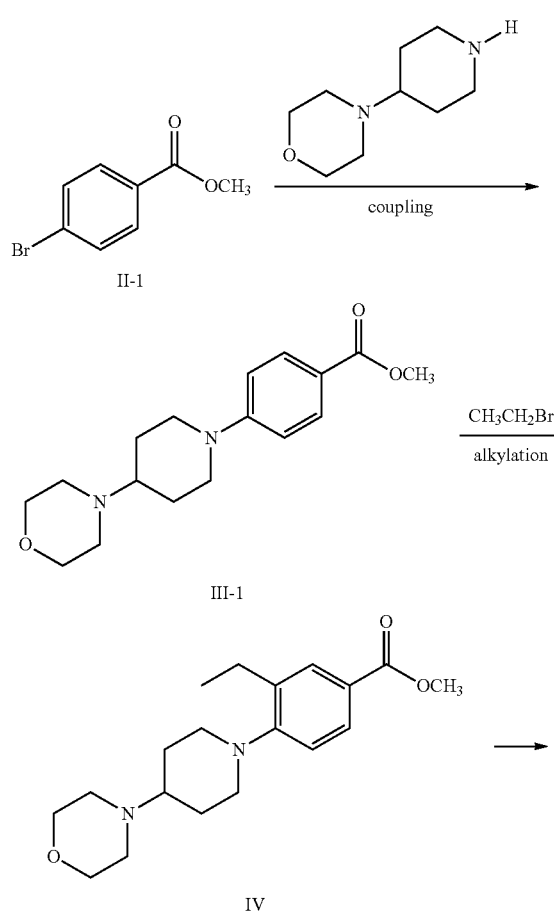

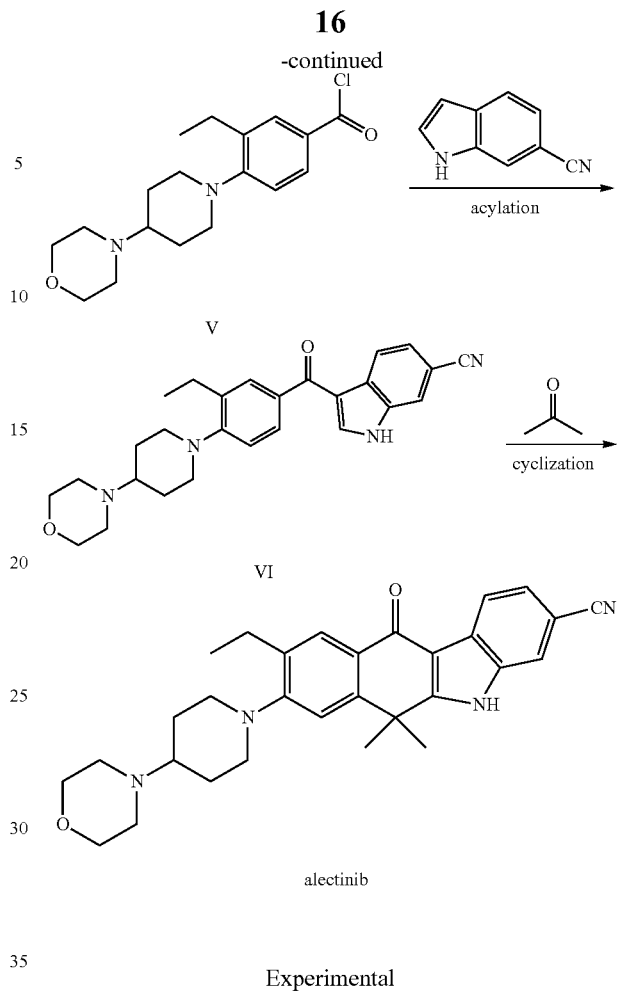

alectinib

Experimental

Detailed experimental parameters suitable for the preparation of alectinib or pharmaceutically acceptable salts thereof according to the present invention are provided by the following examples, which are intended to be illustrative and not limiting.

Unless otherwise noted, all materials, solvents and reagents, including anhydrous solvents such as DMF and DCM, were obtained from commercial suppliers, of the best grade, and used without further purification. All reactions involving air- or moisture-sensitive compounds were performed under nitrogen or argon atmosphere, unless otherwise noted.

The ¹H (400 MHz) and ¹³C NMR (100 MHz) data were recorded on BrukerAVANCE II 400 MHz spectrometer using CDCl₃ or DMSO-D₆ as solvent. The chemical shifts (δ) are reported in ppm and coupling constants (J) in Hz. ¹H NMR spectra was recorded with tetramethylsilane (δ=0.00 ppm) as internal reference; ¹³C NMR spectra was recorded with CDCl₃ (δ=77.00 ppm) or DMSO-D₆ (δ=39.5 ppm) as internal reference.

The synthesis of L1:

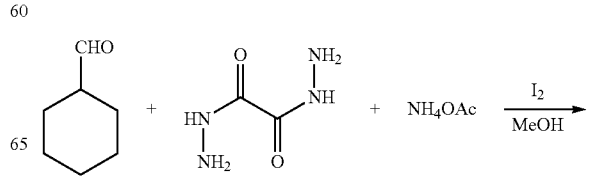

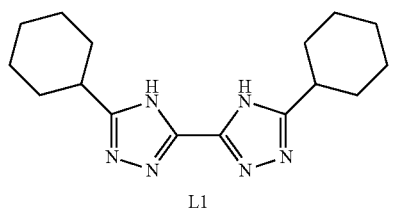

L1

To a solution of cyclohexanecarbaldehyde (11.2 g, 100 mmol), oxalohydrazide (6.5 g, 55 mmol), and ammonia acetate (8.5 g, 110 mmol) in methanol (200 mL), was added iodine (2.5 g, 10 mmol). The reaction mixture was refluxed for 20 h before being filtered. The resulted solid was washed with methanol (50 mL) three times and ether (50 mL), then dried under vacuum to afford desired L1 as yellow solid. Yield: 12 g, 80%. $^1$H NMR (400 MHz, CDCl$_3$) δ 11.12 (brs, 2H), 2.69-2.75 (m, 2H), 1.61-1.86 (m, 8H), 1.33-1.63 (m, 12H). $^{13}$C NMR (100 MHz, CDCl$_3$) δ 163.5, 159.3, 39.5, 33.0, 26.1, 26.4. ESI-TOF-HRMS calculated for C$_{16}$H$_{24}$N$_6$Na (M+Na) 323.1960, found 323.1924.

The synthesis of L6:

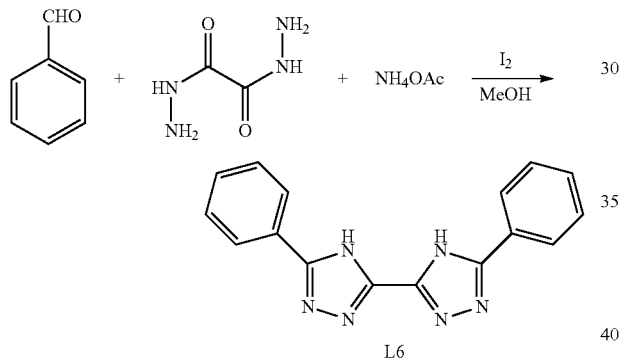

L6

To a solution of benzaldehyde (10.6 g, 100 mmol), oxalohydrazide (6.5 g, 55 mmol), and ammonia acetate (8.5 g, 110 mmol) in methanol (200 mL), was added iodine (2.5 g, 10 mmol). The reaction mixture was refluxed for 18 h before being filtered. The resulted solid was washed with methanol (50 mL) three times and ether (50 mL), then dried under vacuum to afford desired L6 as yellow solid. Yield: 11 g, 77%. $^1$H NMR (400 MHz, CDCl$_3$) δ 11.12 (brs, 2H), 8.05-8.09 (m, 4H), 7.43-7.51 (m, 6H). $^{13}$C NMR (100 MHz, CDCl$_3$) δ 163.5, 157.6, 132.5, 131.1, 129.2, 127.5. ESI-TOF-HRMS calculated for C$_{16}$H$_{12}$N$_6$Na (M+Na) 311.1021, found 311.1003.

The synthesis of L7:

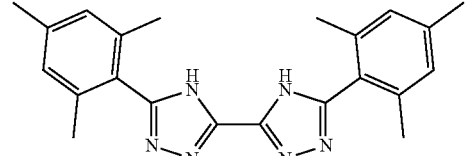

L7

To a solution of 2,4,6-trimethyl-benzaldehyde (14.8 g, 100 mmol), oxalohydrazide (6.5 g, 55 mmol), and ammonia acetate (8.5 g, 110 mmol) in methanol (200 mL), was added iodine (2.5 g, 10 mmol). The reaction mixture was refluxed for 24 h before being filtered. The resulted solid was washed with methanol (50 mL) three times and ether (50 mL), then dried under vacuum to afford desired L7 as yellow solid. Yield: 12 g, 65%. 1H NMR (400 MHz, CDCl$_3$) δ 11.12 (brs, 2H), 7.01 (s, 4H), 2.57 (s, 12H), 2.48 (s, 6H). $^{13}$C NMR (100 MHz, CDCl$_3$) δ 163.5, 157.6, 138.2, 136.1, 128.2, 122.5, 21.9, 19.3. ESI-TOF-HRMS calculated for C$_{22}$H$_{24}$N$_6$Na (M+Na) 395.1960, found 395.1932.

The synthesis of compound of formula III-1 with L1:

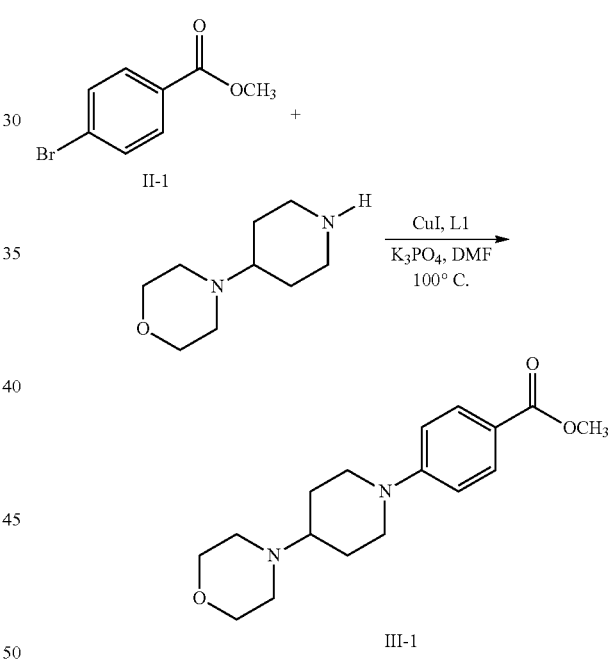

III-1

To a solution of methyl 4-bromobenzoate (21.5 g, 100 mmol), 4-(piperidin-4-yl)morpholine (18.7 g, 110 mmol), and K$_3$PO$_4$ (23.3 g, 110 mmol) in DMF (100 mL), was added CuI (1.9 g, 10 mmol) and L1 (3 g, 10 mmol). The reaction mixture was stirred at 100° C. for 10 h before being partitioned between ethyl acetate (300 mL) and water (100 mL). The combined organics were dried over MgSO$_4$, filtered and concentrated in vacuum to give a crude product, which was purified by flash chromatography (hexane/ethyl acetate 5/1 eluent). Desired compound of formula III-1 was obtained as colorless oil. Yield: 22 g, 73%. $^1$H NMR (400 MHz, CDCl$_3$) δ 7.84 (d, J=7.5 Hz, 2H), 6.93 (d, J=7.5 Hz, 2H), 3.89 (s, 3H), 3.57 (t, J=7.1 Hz, 4H), 3.03-3.16 (m, 4H), 2.59-2.64 (m, 1H), 2.48 (t, J=7.1 Hz, 4H), 1.65-1.73 (m, 2H), 1.40-1.47 (m, 2H). $^{13}$C NMR (100 MHz, CDCl$_3$) δ 165.9, 153.9, 130.8, 123.1, 111.7, 70.4, 67.0, 52.1, 52.0, 51.5, 28.1. ESI-TOF-HRMS calculated for $C_{17}H_{24}N_2NaO_3$ (M+Na) 327.1685, found 327.1648.

The synthesis of compound of formula III-1 with L6:

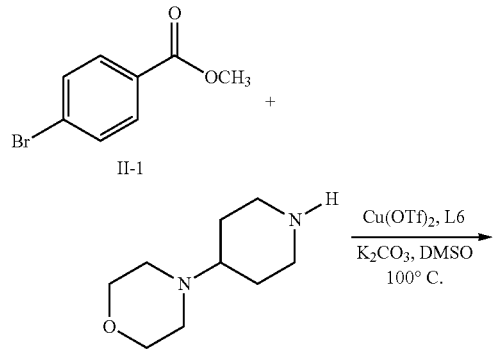

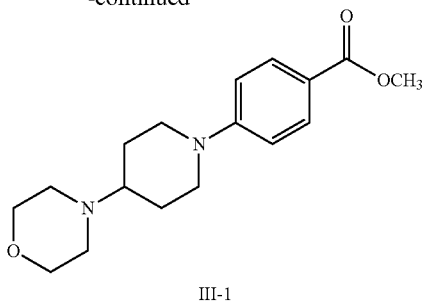

To a solution of methyl 4-bromobenzoate (21.5 g, 100 mmol), 4-(piperidin-4-yl)morpholine (18.7 g, 110 mmol), and $Cs_2CO_3$ (35.8 g, 110 mmol) in $CH_3CN$ (100 mL), was added $Cu(acac)_2$ (2.6 g, 10 mmol) and L7 (3.7 g, 10 mmol). The reaction mixture was stirred at 100° C. for 9 h before being partitioned between ethyl acetate (300 mL) and water (100 mL). The combined organics were dried over $MgSO_4$, filtered and concentrated in vacuum to give a crude product, which was purified by flash chromatography (hexane/ethyl acetate 5/1 eluent). Desired compound of formula III-1 was obtained as colorless oil. Yield: 24 g, 80%.

The synthesis of compound of formula IV:

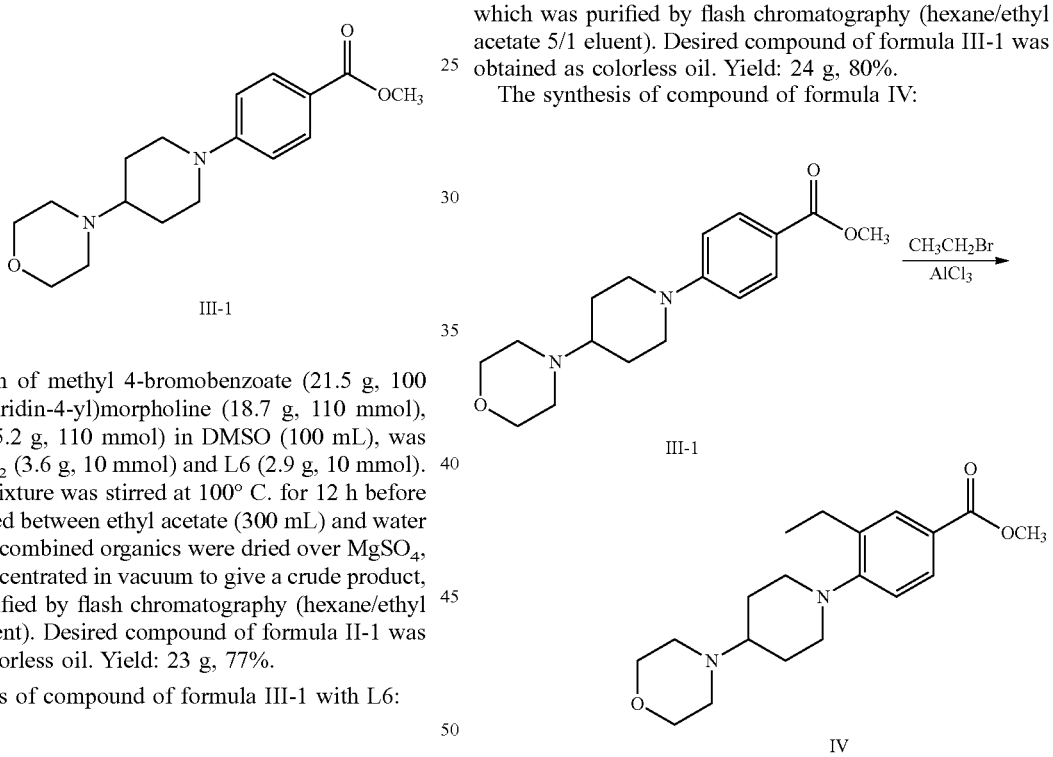

To a solution of methyl 4-bromobenzoate (21.5 g, 100 mmol), 4-(piperidin-4-yl)morpholine (18.7 g, 110 mmol), and $K_2CO_3$ (15.2 g, 110 mmol) in DMSO (100 mL), was added $Cu(OTf)_2$ (3.6 g, 10 mmol) and L6 (2.9 g, 10 mmol). The reaction mixture was stirred at 100° C. for 12 h before being partitioned between ethyl acetate (300 mL) and water (100 mL). The combined organics were dried over $MgSO_4$, filtered and concentrated in vacuum to give a crude product, which was purified by flash chromatography (hexane/ethyl acetate 5/1 eluent). Desired compound of formula II-1 was obtained as colorless oil. Yield: 23 g, 77%.

The synthesis of compound of formula III-1 with L6:

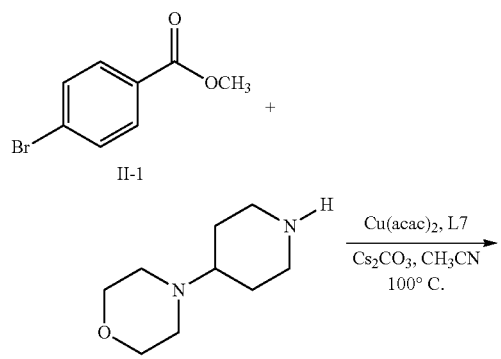

To a stirring mixture of III-1 (15 g, 50 mmol) and bromoethane (5.9 g, 55 mmol), was added $AlCl_3$ (13 g, 100 mmol) in portions. The reaction mixture was stirred at 120° C. for 5 h before being cooled to room temperature. Then DCM (200 mL) was added and the resulted mixture was stirred for another 1 h before ice (200 g) was added. The mixture was partitioned between DCM and water. The combined organics were dried over $MgSO_4$, filtered and concentrated in vacuum to give a crude product, which was purified by flash chromatography (hexane/ethyl acetate 6/1 eluent). Desired compound of formula IV was obtained as colorless oil. Yield: 12 g, 72%. $^1$H NMR (400 MHz, $CDCl_3$) δ 7.69 (s, 1H), 7.50 (d, J=7.5 Hz, 1H), 6.84 (d, J=7.5 Hz, 1H), 3.89 (s, 3H), 3.57 (t, J=7.1 Hz, 4H), 3.03-3.16 (m, 4H), 2.56-2.64 (m, 3H), 2.48 (t, J=7.1 Hz, 4H), 1.65-1.73 (m, 2H), 1.40-1.47 (m, 2H), 1.12 (t, J=8.0 Hz, 3H). $^{13}$C NMR (100 MHz, CDCl$_3$) δ 165.9, 150.3, 129.8, 128.0, 123.5, 119.5, 108.7, 70.4, 67.0, 52.4, 52.0, 51.5, 28.1, 23.7, 14.5. ESI-TOF-HRMS calculated for C$_{19}$H$_{28}$N$_2$NaO$_3$ (M+Na) 355.1998, found 355.1974.

The synthesis of compound of formula V:

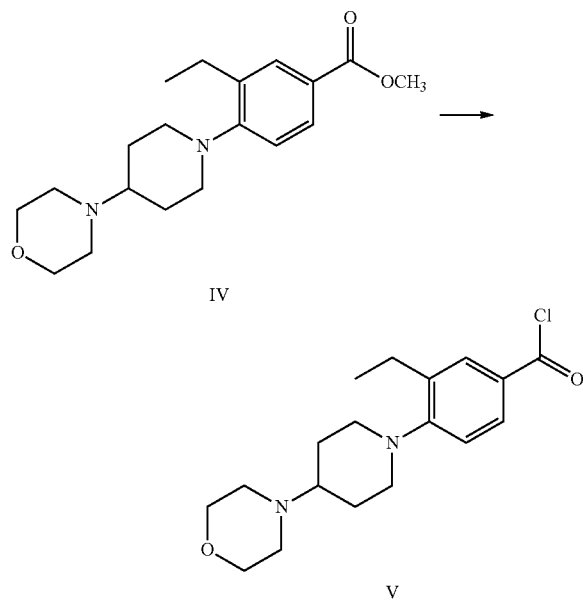

To a stirring mixture of IV (6.6 g, 20 mmol) in the solvents of CH$_3$CN (50 mL) and water (50 mL), was added LiOH (0.5 g, 22 mmol). The reaction mixture was refluxed for 8 h before being cooled to room temperature. The resulted mixture was concentrated to a volume of 60 mL on rotary evaporator. Then THF (80 mL) was slowly added to the reaction crude to obtain a white precipitate, which was filtered, washed with methanol (3×30 mL) and then dried under vacuum. Next, the resulted white solid was dissolved in DCM (100 mL) and cooled to 0° C., then SOCl$_2$ (2.6 g, 22 mmol) was slowly added to the reaction mixture. The reaction mixture was allowed to come to room temperature over 1 h and stirred at room temperature for 4 h. Then all volatiles were removed under vacuum to obtain a crude product of formula V, which was directly used in next step without purification.

The synthesis of compound of formula VI:

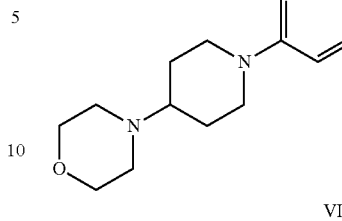

+

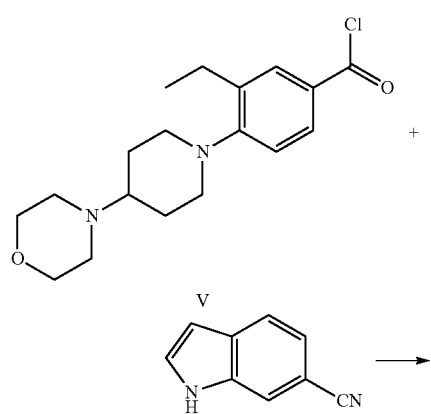

→

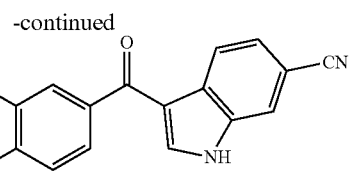

The crude product of formula V obtained from last step was dissolved in DCE (100 mL), to this mixture, was added 6-cyanoindole (2.8 g, 20 mmol) and then AlCl$_3$ (5.2 g, 40 mmol) in portions. The reaction mixture was refluxed for 10 h before being cooled to room temperature and ice (100 g) being added. The mixture was partitioned between DCM and water. The combined organics were dried over MgSO$_4$, filtered and concentrated in vacuum to give a crude product, which was purified by flash chromatography (hexane/ ethyl acetate 4/1 eluent). Desired compound of formula VI was obtained as yellow solid. Yield: 5.2 g, 59% (from compound IV). $^1$H NMR (400 MHz, CDCl$_3$) δ 11.69 (s, 1H), 8.71 (s, 1H), 8.11 (d, J=7.5 Hz, 1H), 7.78 (s, 1H), 7.58 (s, 1H), 7.53 (d, J=7.5 Hz, 1H), 7.36 (d, J=7.5 Hz, 1H), 6.92 (d, J=7.5 Hz, 1H), 3.57 (t, J=7.1 Hz, 4H), 3.03-3.16 (m, 4H), 2.56-2.64 (m, 3H), 2.48 (t, J=7.1 Hz, 4H), 1.65-1.73 (m, 2H), 1.40-1.47 (m, 2H), 1.12 (t, J=8.0 Hz, 3H). $^{13}$C NMR (100 MHz, CDCl$_3$) δ 196.3, 149.3, 136.2, 130.6 129.5, 127.8, 125.9, 125.2, 124.5, 123.7, 123.4, 119.5, 118.6, 114.3, 108.5, 99.5, 70.4, 67.0, 52.4, 52.0, 51.5, 28.1, 23.7, 14.5. ESI-TOF-HRMS calculated for C$_{27}$H$_{30}$N$_4$NaO$_2$ (M+Na) 465.2266, found 465.2234.

The synthesis of alectinib with AlCl$_3$ and CoCl$_3$:

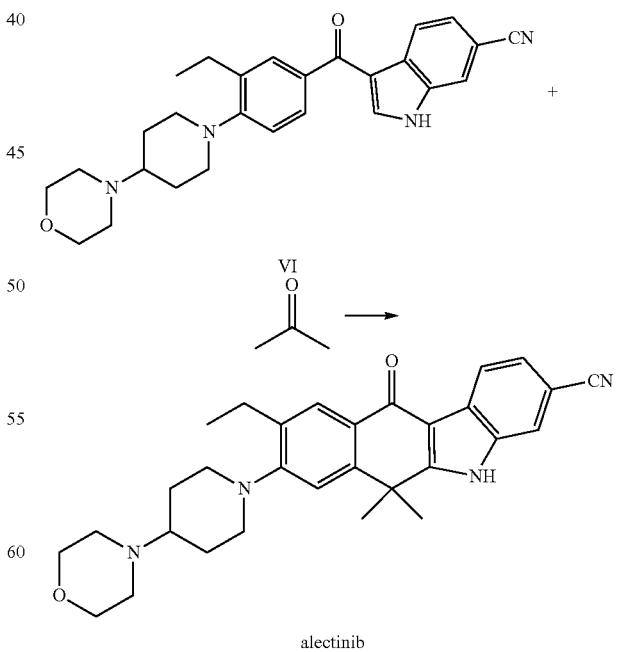

alectinib

To a stirring mixture of VI (4.4 g, 10 mmol) in acetone (20 mL), was added AlCl$_3$ (2.6 g, 20 mmol) and CoCl$_3$ (0.33 g, 2 mmol). The stirring mixture was sealed and maintained at 100° C. for 4 h before being cooled to room temperature. Then DCM (100 mL) was added and the resulted mixture was stirred for another 0.5 h before ice (50 g) was added. The mixture was partitioned between DCM and water. The combined organics were dried over MgSO₄, filtered and concentrated in vacuum to give a crude product, which was recrystallized from hot MeOH (50 mL). The pure product was obtained as an off-white solid. Yield: 3.2 g, 67%.

$^1$H NMR (400 MHz, DMSO) δ 12.46 (s, 1H), 8.21 (d, J=8.2 Hz, 1H), 8.05 (d, J=2.5 Hz, 1H), 7.78 (d, J=2.0 Hz, 1H), 7.53 (dd, J=8.1, 1.8 Hz, 1H), 7.32 (s, 1H), 3.92 (s, 4H), 3.42 (b, 4H), 3.19 (b, 1H), 2.98 (m, J=10.9 Hz, 4H), 2.72 (q, J=7.6 Hz, 2H), 1.82 (s, 4H), 1.69 (d, J=45.9 Hz, 6H), 1.24 (t, J=7.6 Hz, 3H). $^{13}$C NMR (100 MHz, DMSO) δ 179.73, 150.81, 150.01, 146.65, 142.65, 136.73, 132.31, 131.85, 127.16, 124.91, 122.10, 120.50, 116.91, 11.89, 105.11, 100.10, 76.81, 72.41, 66.81, 66.41, 36.65, 30.47, 28.22, 27.92, 15.92; ESI-TOF-HRMS calculated for $C_{30}H_{35}N_4O_2$ (M+H) 483.2755, found 483.2728.

The synthesis of alectinib with MgCl₂ and CrCl₃:

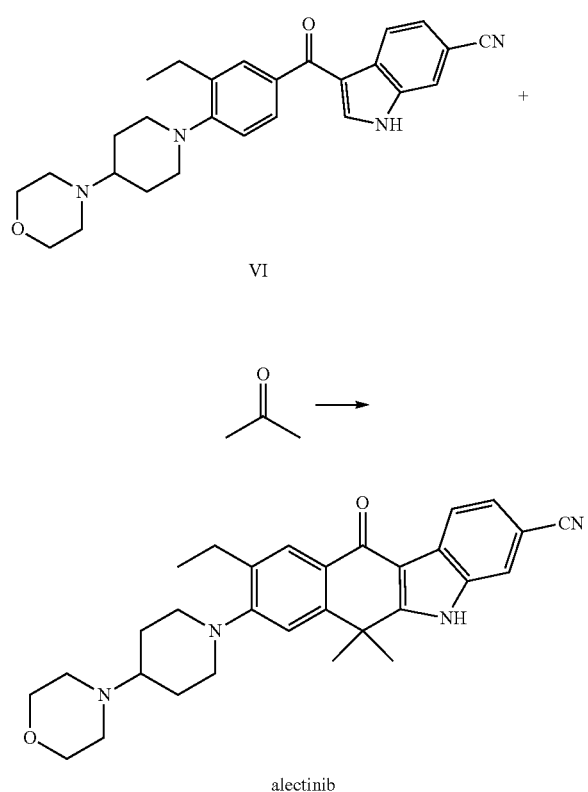

alectinib

To a stirring mixture of VI (4.4 g, 10 mmol) in acetone (20 mL), was added MgCl₂ (1.9 g, 20 mmol) and CrCl₃ (0.32 g, 2 mmol). The stirring mixture was sealed and maintained at 100° C. for 4 h before being cooled to room temperature. Then DCM (100 mL) was added and the resulted mixture was stirred for another 0.5 h before ice (50 g) was added. The mixture was partitioned between DCM and water. The combined organics were dried over MgSO₄, filtered and concentrated in vacuum to give a crude product, which was recrystallized from hot MeOH (50 mL). The pure product was obtained as an off-white solid. Yield: 3.0 g, 63%.

The synthesis of alectinib with 4 Å molecular sieves and CoCl₃:

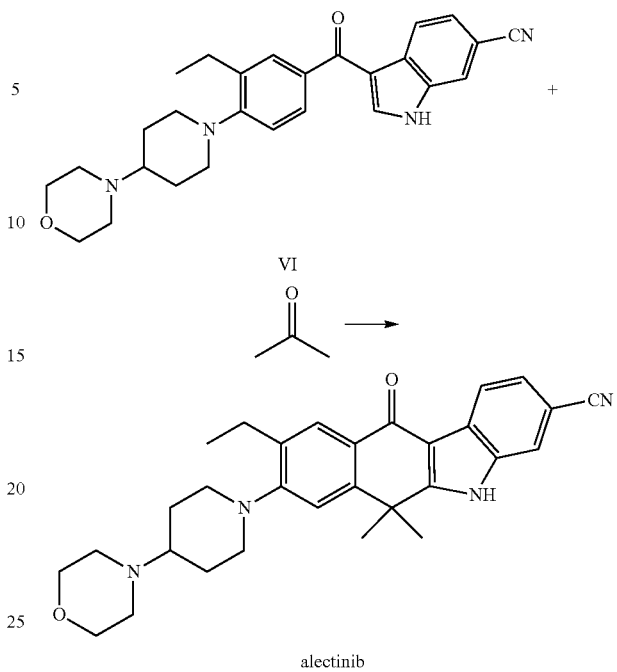

alectinib

To a stirring mixture of VI (4.4 g, 10 mmol) in acetone (20 mL), was added 4 Å molecular sieves (5 g) and Co(NO₃)₃ (0.48 g, 2 mmol). The stirring mixture was sealed and maintained at 100° C. for 4 h before being cooled to room temperature. Then DCM (100 mL) was added and the resulted mixture was stirred for another 0.5 h before ice (50 g) was added. The mixture was partitioned between DCM and water. The combined organics were dried over MgSO₄, filtered and concentrated in vacuum to give a crude product, which was recrystallized from hot MeOH (50 mL). The pure product was obtained as an off-white solid. Yield: 3.3 g, 69%.

The invention claimed is:

1. A method for manufacturing alectinib of Formula I,

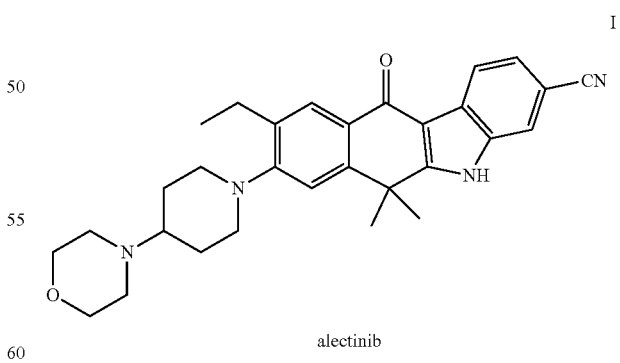

alectinib which comprises the steps of:

Step 1: Reacting a compound of formula II with 4-(piperidin-4-yl)morpholine in the presence of a base, a copper catalyst and a ligand to form the compound of formula III,

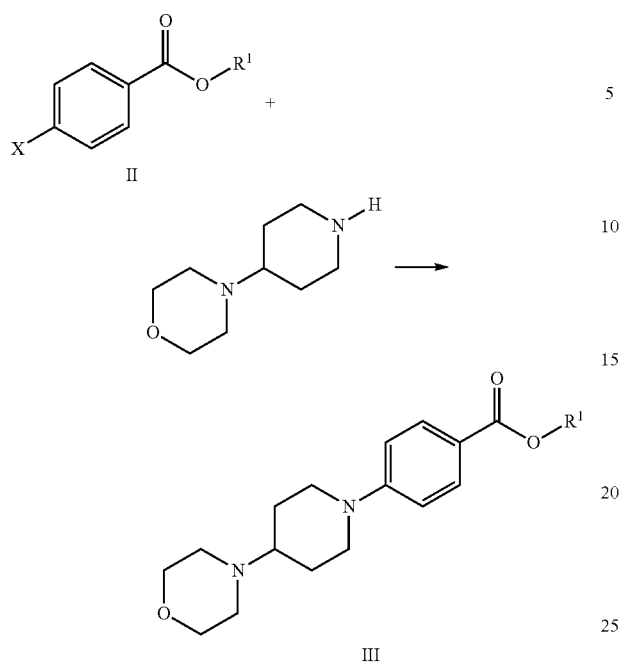

wherein X is selected from the group consisting of —Cl, —Br, —I, —OSO$_2$Ar, and —OSO$_2$CF$_3$; R$^1$ is selected from the group consisting of —CH$_3$, —CH$_2$CH$_3$, —C(CH$_3$)$_3$; the ligand is formula (LI)

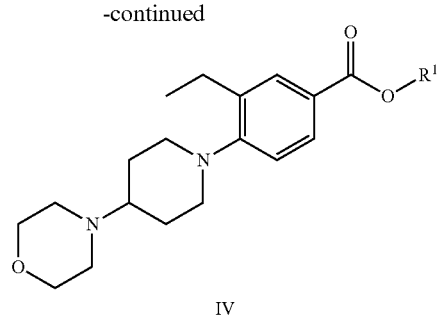

Step 2: Reacting a compound of formula III with CH$_3$CH$_2$Y in the presence of a Lewis acids catalyst to form a compound of formula IV,

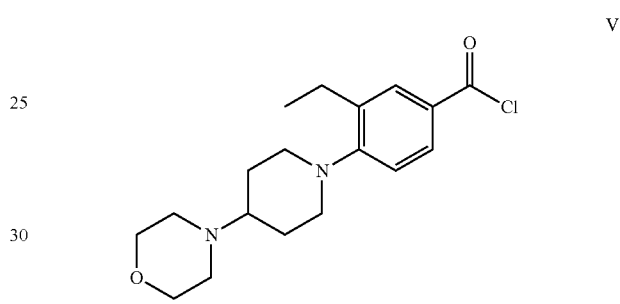

wherein Y is selected from the group consisting of —Cl, —Br and —I,

Step 3: hydrolysis of formula IV resulting in corresponding carboxylic acid, which was then converted to a compound of formula V,

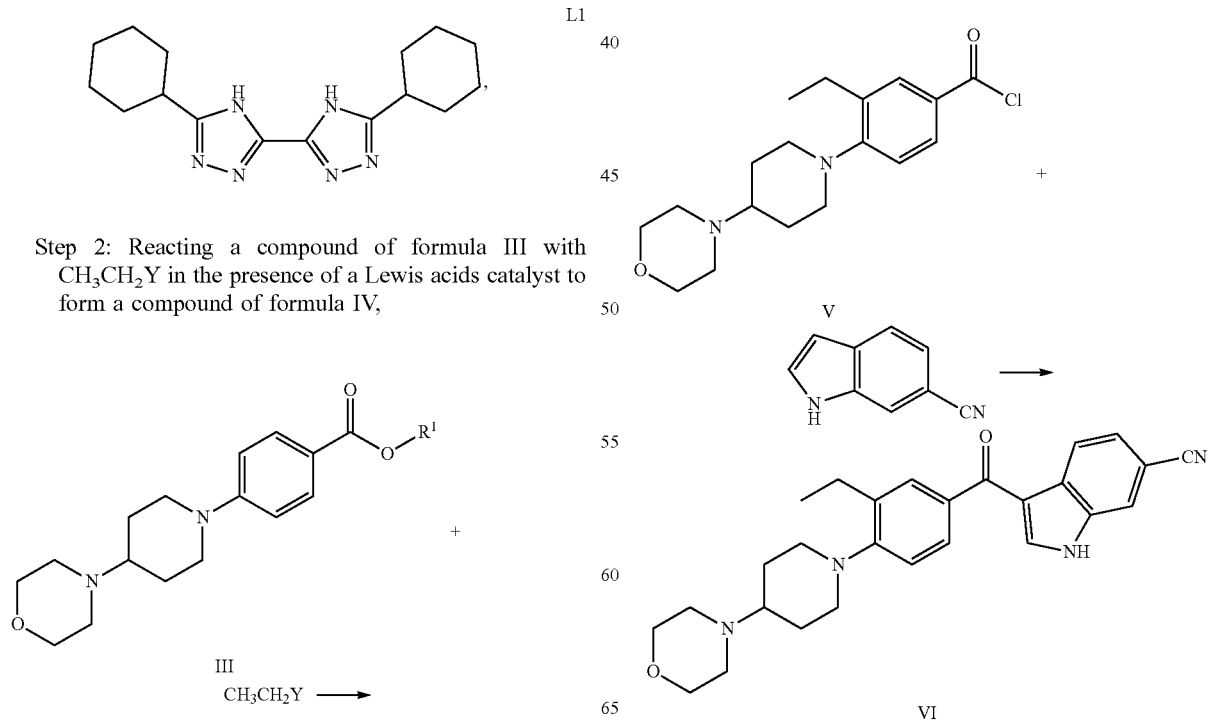

Step 4: Reacting a compound of formula V with 6-cyanoindole in the presence of a Lewis acids catalyst to form a compound of formula VI, Step 5: Reacting a compound of formula VI with acetone in the presence of a dehydrating reagent and a catalyst to form the alectinib, wherein the dehydrating reagent is selected from $MgCl_2$, $AlCl_3$, $CaCl_2$, 4 Å molecular sieves, and silica gel; the catalyst is selected from $CrCl_3$, $CrF_3$, $CrBr_3$, $Cr(NO_3)_3$, $CoCl_3$, $CoF_3$, $CoBr_3$, $Co(NO_3)_3$.

2. The method of claim 1, wherein the above process is carried out by isolating all intermediate compounds, or the process is carried out without isolating intermediate compound of formula III, IV, V and VI, or the above process is carried out as a one-pot reaction.

3. The method of claim 1, wherein the base of step 1 is selected from TEA, DBU, DIPEA, KOH, $K_2CO_3$, NaOH, $Na_2CO_3$, $Cs_2CO_3$, CsOH, $K_3PO_4$, $K_2HPO_4$, $Na_3PO_4$, and $Na_2HPO_4$.

4. The method of claim 1, wherein the copper catalyst of Step 1 is selected from CuI, CuCl, CuBr, $Cu_2O$, $Cu(acac)_2$ $CuCl_2$, $CuBr_2$, $CuI_2$, $Cu(OAc)_2$, $Cu(OTf)_2$, $Cu(ClO_4)_2$, and $CuSO_4$.

5. The method of claim 1, wherein the Lewis acid catalyst of Step 2 is selected from $AlCl_3$, $BeCl_2$, $CdCl_2$, $BF_3$, $BBr_3$, $GaCl_3$, $AlBr_3$, $FeCl_3$, $TiCl_4$, $SnCl_4$, $SbCl_5$, lanthanide trihalide, and alkylaluminum halide.

6. The method of claim 1, wherein the Lewis acid catalyst of Step 4 is selected from $AlCl_3$, $AlBr_3$, lanthanide triflate, zeolites, protic acid, $FeCl_3$, $ZnCl_2$, polyphosphoric acid.

\* \* \* \* \*